United States Patent [19]

Kendall et al.

[11] Patent Number: 5,260,283
[45] Date of Patent: Nov. 9, 1993

[54] METHOD FOR ALTERING EXCRETION OF ESTROGENS OR LIPIDS IN MAMMALS

[75] Inventors: Marcia E. Kendall, Somerset, N.J.; Leonard A. Cohen, Chappaqua, N.Y.

[73] Assignee: American Health Foundation, Valhalla, N.Y.

[21] Appl. No.: 885,530

[22] Filed: May 19, 1992

[51] Int. Cl.$^5$ ............................................. A61K 31/715
[52] U.S. Cl. ........................................ 514/57; 514/60; 514/892
[58] Field of Search .................. 424/195.1; 514/60, 57, 514/892

[56] References Cited

PUBLICATIONS

National Research Council, Committe on Diet and Health. Diet and Health. Implications for Reducing Chronic Disease Risk. Washington, D.C. National Acad. Press, 1989.
Van't Veer, P., et al. Int. J. Cancer 45:825–828 (1990).
Rose, D. P., Cancer Surveys 5(3):671–687 (1986).
Lubin, F., et al. JNCI 77:605–612 (1986).
Rose, D. P., Nutrition and Cancer 13 (1 and 2):1–8 (1990).
Adlercreutz, H., et al. Proceedings of the Symposium on the Analysis of Steroids, Eger, Hungary (1981).
Adlercreutz, H., Gastroenterology 86:761–766 (1986).
Adlercreutz, H., et al. Prog. Cancer Res. Ther. 35:409–412 (1988).
Armstrong, B. K., et al. JNCI 67:761–767 (1981).
Goldin, B. R., et al. Am. J. Clin. Nutr. 44:945–953 (1986).
Goldin, B. R. et al. N. Eng. J. Med. 307:1542–1547 (1982).
Gorbach, S. L., and Goldin, B. R. Prevent. Med. 16:525–531 (1987).
Fentiman, I. S. et al. Nutr. Cancer 11:101–106 (1988).
Barbosa, J. C., et al. Am J. Clin. Nutr. 51:798–803 (1990).
Chan, P. C., et al. JNCI 59:1279–1283 (1977).
Bieri, J. G., et al. J. Nutr. 107:1340–1348 (1977).
Kohigashi, K., et al. Jpn. J. Cancer Res. (Gann) 79:1335–1339 (1988).
Fotsis T., and Adlercreutz, H. J. Steroid Biochem. 28(2):203–213 (1987).
Shultz, T. D. and Howie, B. J. Cancer 8:141–147 (1986).
Porter, L. E., et al. Gastroenter. 84:704–712 (1984).
Aten, R. F., et al. Endocrinol. 131:1629–1635 (1978).
Powell-Jones, W., et al. J. Steroid Biochem. 13:219–229 (1980).
Southgate, D.A.T., and Durnin, J.V.G.A. Brit. J. Nutr. 24: 517–535 (1970).
24. Kelsay, J. L., et al., Am. J. Clin. Nutr. 31:1149–1153 (1978).
Heber, David et al. (Mar./Apr. 1991) Nutrition 7:137.
Cohen, L. A., et al. J. Natl. Cancer Inst. (1991) 83:496.
Rose, David P. Am. J. Clin. Nutr. (1991) 54:520–5.
Arts, Cor J. M., J. Steroid Biochem. Molec. Biol. (Aug. 30, 1991) 39:193–202.
Cohen, L. A. et al. (Abstract) Presented Poster session Oct. 1990.
Woods, Margo N. Am. J. Clin. Nutr. (1989) 49:1179–83.
Kendall, M. E., et al. 73rd Annual Endocrine Society Meeting Washington, D.C. published May 20, 1991.

Primary Examiner—John W. Rollins
Attorney, Agent, or Firm—Felfe & Lynch

[57] ABSTRACT

Wheat bran fiber is used to alter the enterohepatic recirculation of estrogens leading to an increased fecal excretion of estrogens together with a decrease in urinary excretion of estrogens. Increased lipid excretion is also found. Thus wheat bran fiber is useful to remove estrogen and lipid in mammals.

7 Claims, 8 Drawing Sheets

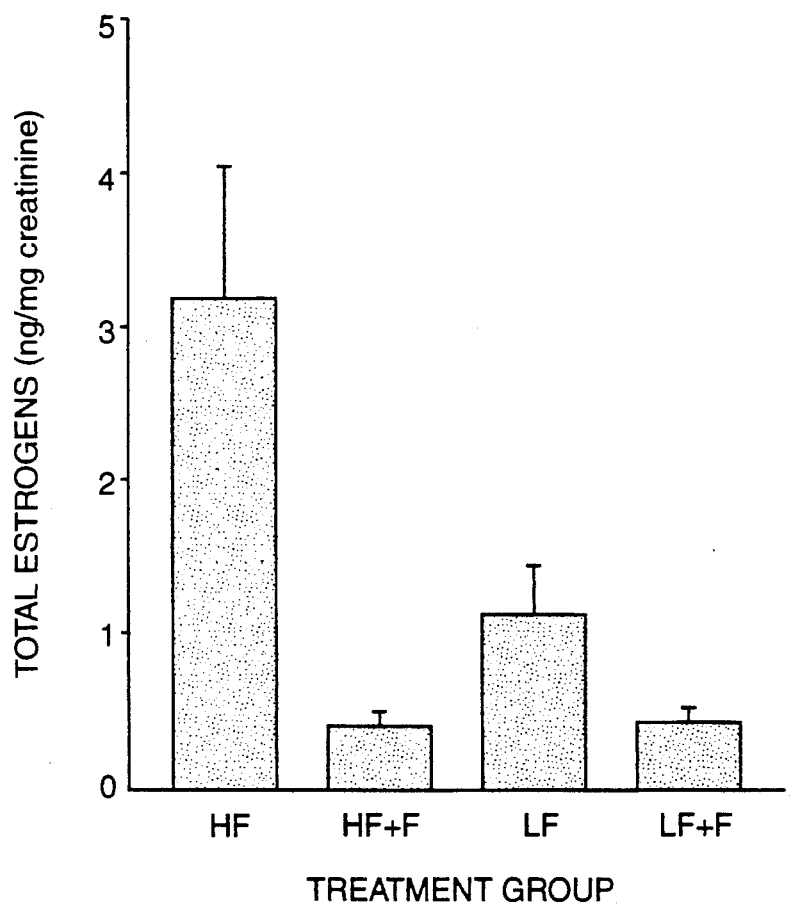

METHOD FOR ALTERING EXCRETION OF ESTROGENS OR LIPIDS IN MAMMALS

This work was done in part using government funding under Public Health Service grant CA-176613 from the National Cancer Institute. Therefore, the United States Government may have certain rights in the invention.

This invention concerns a method for altering the excretion of lipids and/or estrogens in mammals using a diet supplemented with soft white wheat bran.

SUMMARY

The present invention concerns a method for altering the excretory metabolism of estrogens by SWWB supplementation in the diet resulting in decreased urinary excretion of conjugated estrogens, associated with an increase in fecal excretion of unconjugated estrogens. It was found that significantly more $^3H$ estrone ($E_1S$) and $^3H$ estradiol ($E_2$) as well as radiolabelled triglyceride ($^3H$ triolein) were bound in vitro to the SWWB than to the purified cellulose used in the standard animal diets. Twenty-four hour fecal lipid excretion was increased in both fiber supplemented groups compared to controls.

DESCRIPTION OF THE FIGURES

FIG. 4 Effect of dietary wheat bran supplementation on 24 hr urinary total ($E_1+E_2$) estrogen levels. Urine was obtained from 4-5 rats/group while the rats were in metabolism cages. Assays were performed using a kit obtained from ICN/RSL. Data points represent mean±SE. The four dietary groups were: HF=high fat (23.5% corn oil); HF+F=high fat plus fiber (10% soft white wheat bran); LF= low fat (5% corn oil); and LF+F=low fat plus fiber (10% soft white wheat bran). The HF+F and LF+F groups were significantly ($p<0.05$) less than their respective nonsupplemented control group and the LF group was significantly ($p<0.05$) less than the HF group.

DESCRIPTION

Figure 1:
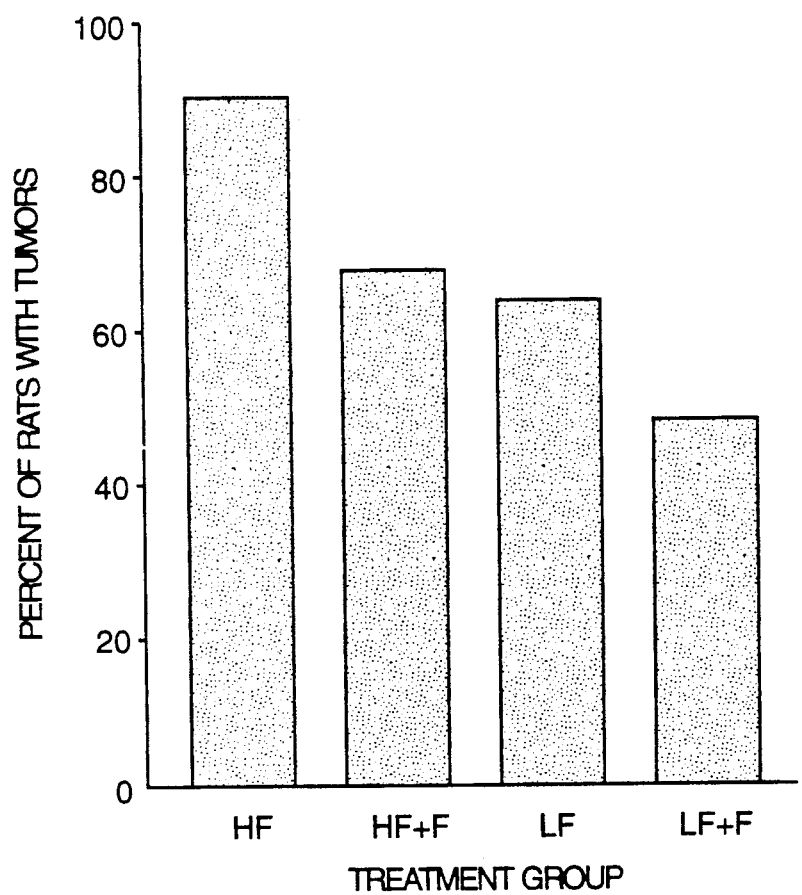
FIG. 1 Effect of dietary wheat bran supplementation on mammary tumor incidence. Thirty rats were in each dietary group. Data points represent mean±SE. The four dietary groups were: HF=high fat (23.5% corn oil); HF+F=high fat plus fiber (10% soft white wheat bran); LF=low fat (5% corn oil); and LF+F=low fat plus fiber (10% soft white wheat bran). The HF+F, LF, and LF+F groups were all significantly ($p<0.01-0.001$) less than the HF alone group.

List of Abbreviations cER  cytosolic estrogen receptor
ER   estrogen receptor
$E_1$   estrone
$E_1S$  estrone sulfate
$E_2$   estradiol
$E_3$   estriol
HF   high fat
HF+F   high fat plus fiber
LF   low fat
LF+F   low fat plus fiber
nER  nuclear estrogen receptor
NMU  N-nitrosomethylurea
SHBG  sex hormone binding globulin
SWWB  soft white wheat bran
TDF  total dietary fiber
AACC  American Association of Cereal Chemists There is currently much interest in diet as it relates to breast cancer risk (1). Several epidemiological studies suggest an inverse relation between fiber intake and the incidence of breast cancer (2-4). (See Rose (5) for review). Adlercreutz, et al. (6-8) proposed the hypothesis that fiber may protect against breast cancer by altering the metabolism and excretion of estrogens (which are known to be involved in mammary tumor development) or by acting as a source of dietary antiestrogen. Subsequently, a number of population studies (9-14) have compared vegetarian (low risk) and nonvegetarian (high risk) women to evaluate the effects of diet on circulating, urinary, and fecal estrogen concentrations.

The results of these studies in vegetarian women regarding plasma estrogens have been inconsistent, but have shown a decrease in urinary and an increase in fecal estrogens. This suggests that dietary fiber may act by influencing the enterohepatic recirculation of estrogens.

Dietary intervention studies have focused attention on the effect of dietary fiber on circulating estrogen levels. Woods, et al. (15) reported that serum $E_1$ and $E_2$ were unchanged in a small group of healthy women consuming a low fat, high fiber diet for 8-10 weeks after 4 weeks on a typical Western diet (high fat, low fiber), but their estrone sulfate ($E_1S$) levels were significantly decreased. In another study, Heber, et al. (16), in a short term (22 days) experiment studying healthy postmenopausal women consuming an extremely low fat (10%), high fiber diet found a significant reduction in serum $E_2$. It is unclear if the observations reported in these studies were due to decreased fat consumption, increased fiber consumption, or both. Woods continuously varied the diet of the subjects and Heber was concerned mainly with weight loss and did not control diet or diet fiber content. However, a major problem with these studies is that the diet composition of the populations studied varied widely making direct comparisons difficult. In one case, for example (10), the fiber content of the vegetarian diet was actually similar to that of the nonvegetarians while the fat content of the diet was one half that of the nonvegetarians; consequently, the changes in urinary and fecal excretion patterns in that study must be attributed to differences in the fat rather than the fiber content of the diet.

Intervention studies (15-17) have focused on changes in circulating levels of estrogens in women consuming fiber supplemented diets over relatively short periods of time. While these studies suggested that fiber supplementation lowers serum estrogen levels, they too are not entirely consistent with one another. For example, Woods, et al. (15) reported that consumption of a fiber supplemented diet had little or no effect on circulating $E_1$ or $E_2$, but markedly suppressed $E_1S$, a storage or transport form of estrogen; and Rose, et al. (17) noted that a wheat bran supplemented diet, but not oat or corn bran supplementation, in 62 healthy premenopausal women, lowered serum $E_1$ and $E_2$ after 2 months on the diet. Therefore, the estrogen measured and the type of fiber supplemented must be accounted for in any explanation of the effect of fiber on estrogen metabolism. This definitive evidence is needed for the effect of supplementary fiber on circulating or systemic estrogen levels since the above work is not consistent.

Previously we reported that supplemental SWWB caused a significant reduction in mammary tumorigenesis in the NMU-induced rat mammary tumor model (18). This animal model was used because: 1) diet and other environmental variables are easily controlled, 2) the tumor obtained closely models human breast cancer, and 3) the F-344 rat exhibits low levels of genetic variability. In the present study, we used the NMU model as a tool to explore the mechanisms by which dietary fiber exerted its protective effects on mammary tumorigenesis. The parameters analyzed included: (1) circulating 17β-estradiol and progesterone; (2) hepatic cER and nER protein; (3) urinary total estrogens; (4) fecal total estrogens; and (5) total fecal lipid. Additionally, to determine whether supplementary fiber might directly bind hormones or lipid, experiments using radiolabelled tracers were conducted.

It will be understood that the specification and examples illustrate but do not limit the present invention. Other embodiments within the spirit and scope of the invention will suggest themselves to those skilled in the art.

EXAMPLE 1

One hundred twenty virgin female inbred F-344 rats, 28 days of age (Charles River Breeding Laboratories, North Wilmington, MA) were used for these studies. The animals were housed and cared for in accordance with institutional guidelines. Upon arrival they were quarantined for 10 days and then housed in a room with controlled temperature (24°±2° C.), light (12 hour light/dark cycle), and humidity (50%). They were housed 3 per cage in plastic cages with hardwood bedding. Food (in powdered form) and water was provided ad libitum. In order to prevent food scattering, "J"-type feeders (Lab Products, Maywood, N.J.) were used. The animals were assigned (based on body weight) to 4 groups of 30 each by accepted randomization procedures (19) and then observed daily throughout this study. On day 50 of age, all rats received a single dose (37.5 mg/kg of body weight) of N-nitrosomethylurea NMU; CAS 684-93-5, Ash-Stevens, Inc., Detroit, Mich.) by tail vein injection. NMU was dissolved in a few drops of 3% acetic acid and diluted with distilled water to give a stock solution of 10 mg/ml, which was administered within 2 hrs. of preparation (20). The animals were fed the NIH-07 diet (Zeigler Bros., Gardners, Pa.) (21) until day 53 of age at which time they were switched to the American Institute of Nutrition diet (AIN-76A), which contained fiber in the form of a purified wood derived cellulose product (alphacel). This diet was supplemented with 10% (wt/wt) SWWB (98% insoluble) or nonfiber supplemented in both the low fat (10% calories as fat) and high fat (40% calories as fat) conditions, thus yielding 4 dietary groups (see Table 1). Certified lots (with documentation of specific components) of SWWB were obtained from the American Cereal Chemists Association (St. Paul, Minn.) (see Table 2). The control diets contained 5% and the test diets 10% total dietary fiber (TDF). The rats remained on these diets until the end of the study (5 wks). Six rats from each group were placed in individual metabolism cages for 4 days between weeks 10 and 11 to obtain 24 hr urine and fecal samples after a 2-3 day adjustment period.

The composition of SWWB is as follows:

| AACC CERTIFIED WHEAT BRAN (Values on "as is" basis) | | |
|---|---|---|
| Assay | 12/1/89 Soft White | Method |
| Crude fiber | — | AOAC 7.071 |
| *Protein (N × 6.31) | 16.41% | AACC 46-08 |
| Moisture | 6.44% | AACC 44-40 |
| Fat | 6.80% | AOAC 14.019 |
| Ash | 6.54% | AACC 08-01 |
| Acid Detergent Fiber | — | AOAC 7.074 |
| Neutral Detergent Fiber | 38.80% | AACC 32-20 |
| Total Dietary Fiber | 44.54% | AOAC 43.A14 |
| Lignin | — | AOAC 7.077 |
| Pectin | 2.3% | C |
| Water Holding Capacity | 1.10 g/g | AACC 56-20 |
| Starch | 11.10% | AACC 76-11 |
| Pentosans | — | AACC 52-10 |
| Carbohydrate, Total | 63.80% | By Calculation |
| Thiamine (B1) | 0.64 mg/100 g | AOAC 43.024 |
| Riboflavin (B2) | 0.44 mg/100 g | AOAC 43.044 |

-continued

AACC CERTIFIED WHEAT BRAN
(Values on "as is" basis)

| | | |
|---|---|---|
| Niacin | 28.94 mg/100 g | AOAC 43.056 |
| Pyridoxine (B6) | 0.11 mg/100 g | D |
| Pantothenic Acid | 1.70 mg/100 g | AOAC 43.200 |
| Vitamin E | 6.20 mg/100 g | D |
| Arsenic | 0.65 ppm | AOAC 25.001 |
| Cadmium | 0.20 ppm | AACC 40-70 |
| Lead | <.05 ppm | AACC 40-70 |
| Mercury | 0.01 ppm | AOAC 25.131 |
| Calcium | 110.0 mg/100 g | AOAC 2.109 |
| Copper | 1.46 mg/100 g | AACC 40-70 |
| Iron | 14.60 mg/100 g | AACC 40-70 |
| Magnesium | 579.0 mg/100 g | AACC 40-70 |
| Phosphorus | 1.60% | AOAC 7.125 |
| Potassium | 1.62% | AACC 40-70 |
| Sodium | 11.0 mg/100 g | AACC 40.70 |
| Zinc | 9.98 mg/100 g | AACC 40.70 |
| Aflatoxin | <1 ppb | E |
| Aerobic Plate Count | 8600 ct/g | AACC 42-11 |
| Yeast | <10 ct/g | |
| Mold | 850 ct/g | AACC 42-50 |
| Coliforms | <3 ct/g | AACC 42-15 |
| Insect Fragments | 0 ct/50 g | AACC 28-60 |
| Rodent Hairs | 0 ct/50 g | AACC 28-60 |
| Pesticides | 0.1 ppm Malathion | AACC 60-60 |

| Granulation - Rotap | White |
|---|---|
| On US #10 (Sieve size) | 0.6% |
| On US #12 | 1.9 |
| On US #14 | 7.4 |
| On US #16 | 12.6 |
| On US #18 | 12.0 |
| On US #20 | 14.4 |
| On US #30 | 25.2 |
| On US #40 | 17.1 |
| On US #50 | 4.6 |
| On US #60 | 1.3 |
| On US #70 | 0.8 |
| Thru US #70 | 1.6 |

*Protein Conversion Factor Taken From "Energy Value of Foods . . . basis and derivation" USDA Handbook No. 74, 1973

The above data summarizes analyses of soft white wheat bran as performed by Medallion Laboratories of St. Paul, Minn. for the AACC. The bran has been processed through an enzyme deactivation steamer system and packaged in poly bags in a corrugated container at five pounds per box. The bran is stored at zero degrees Fahrenheit in Minneapolis, Minn.

A. Abbreviations: mg-milligrams
ppm-parts per million
ppb-parts per billion

B. AOAC methods are found in The Official Methods of Analysis
of AOAC published by The Association, 14th edition (1984)
AOAC-Association of Official Analytical Chemists (now AOAC
International). AACC Methods as in Approved Methods of the
Amer Association of Cereal Chemists, 8th Ed. as updated
through 1991. (The Association, St. Paul, Minn. 1983).

C. Reported as % calcium pectate. Medallion Labs modified
procedure for pectin in the presence of protein.

D. Vitamins E, A and B6 by HPLC Method by Medallion Labs. Also
see Egberg, DeVries & Heroff. "Concurrent Analysis of
Vitamins A and E by Reverse Phase HPLC" in Liquid
Chromatographic Analysis of Food and Beverages Vol. II
Academic Press, 1979 ed. George Charlambous. Vitamin B6 by
AOAC Method 96.15 (15th Ed) without column.

E. Aflatoxins by HPLC (high performance liquid chromatograph).

EXAMPLE II

Serum Collection and Hormone Assays

Blood was collected in evacuated sterile Autosep tubes (Terumo Medical, Elkton, Md.) at the termination of the study by cardiac puncture under ketamine anesthesia. Serum was separated by centrifugation and stored at −20° C. Rats were then euthenized by carbon dioxide inhalation and livers excised, weighed, sectioned, and stored at −70° C. until assayed. Serum 17$\beta$-estradiol and progesterone levels were determined by specific radioimmunoassays with the use of reagents from ICN/RSL (Costa Mesa, Calif.).

EXAMPLE III (ER) Assays

Estrogen Receptor (ER) Assays

Cytosolic ER (cER) and nuclear ER (nER) assays were performed on liver homogenates using the Abbott ER-EIA monoclonal kit (Abbott Laboratories, North Chicago, IL). The cytosolic and nuclear preparations were processed as described by Kohigashi, et al. (22). Briefly, the cER was prepared by homogenizing 0.5–0.7 g of tissue in 6 volumes of Tris-EDTA-dithiothreitol (TED) buffer followed by centrifugation at 25,000×g for 20 min. The supernatant was then centrifuged at 105,000×g for 60 min. This resulting supernatant was used for the ER-EIA which was performed exactly as described in the product insert. Protein determinations on the cytosolic preparation, using kits purchased from Sigma Chemical Company (St. Louis, Mo.) were made spectrophotometrically at 640 nm. The tissue for the nER assay was homogenized as described above and centrifuged at 800×g for 15 min. The pellet comprising the nuclear fraction was washed 4 times by resuspension in TED buffer with 15 min centrifugations at 800×g between each wash step. The nER was then extracted from the washed pellet by resuspension in TED buffer containing 0.5M NaSCN. This was allowed to incubate at 4° C. for 60 min with brief vortexing at 15 min intervals. The suspension was then centrifuged at 105,000×g and an aliquot of the resulting supernatant was used for the ER-EIA.

EXAMPLE IV

Urinary Estrogens Extraction And Assay

Twenty-four hour urines were collected while the animals were in the metabolism cages. (F-344 rats excrete approximately 10–15 ml of urine/24 hr). Urine was collected, frozen, and stored at −20° C. until analyzed. Urine was prepared for estrogen assay as follows: 0.3 ml of urine was added to 0.7 ml of H$_2$O and 0.1 ml acetate buffer (pH 4.5). To this mixture was added 0.1 ml $\beta$-glucuronidase. This mixture was incubated at 37° C. for 24 hrs in a shaking water bath. The deconjugated estrogens were then extracted from the mixture by adding 5 ml ether, mixing, and centrifuging. The ether layer was removed and dried under nitrogen. The remaining residue was brought up in buffer and assayed for total estrogens by [$^3$H]RIA procedures (ICN/RSL, Costa Mesa, Calif.).

EXAMPLE V

Fecal Estrogens Extraction and Assay

Twenty-four hour obtained while the animals were in the metabolism cages. Fecal $E_1$ plus $E_2$ was assayed by a modification of the procedure described by Adlercreutz, et al. (6) and Fotsis (23). Estrogens were extracted by homogenizing 250 mg of feces with a tissue homogenizer in 10 ml of ethanol:acetone (9:1). The homogenate was then passed through a scintered glass filter to remove all particulates. The filter was rinsed 3× with ethanol:acetone (9:1) and the filtrate evaporated to dryness using a rotary evaporator. Fifty ml of 70% methanol was added to the dried residue, mixed completely, and stored at −20° C. overnight. A small precipitate formed and was removed by centrifugation at 2500 rpm for 15 min at 4° C., after which the clear supernatant was evaporated to near dryness. Approximately 5-7 ml remained to which was added an equal volume (5-7 ml) of acetate buffer (pH 4.5). Forty-five ml of ethyl ether was added to the flask, mixed well and the contents added to a separatory funnel. Upon separation, the clear component (containing the estrogens) was removed and evaporated to dryness in a hood using nitrogen.

The extract was then subjected to two chromatographic steps to remove interfering color compounds. It was first brought up in 70% methanol, chromatographed through a DEAE-A25 column (4.5 cm), the methanol evaporated under nitrogen, the residue brought up in methanol:toluene (9:91), and chromatographed on a LH-20 column. The eluate was evaporated to dryness and brought up in 20 μl of ethanol and assayed for total estrogens by [$^3$H]RIA procedures (ICN/RSL, Costa Mesa, Calif.).

EXAMPLE VI

Fecal Lipid Extraction

Twenty-four hour fecal samples were analyzed for total lipid content using standard gravimetric techniques (Soxhlet extraction). One gram of feces was refluxed with 300 mls alcohol:anhydrous ether (2:1) in a Soxhlet apparatus for 24 hrs. The sample was then completely dried and the lipid content determined gravimetrically by subtracting the extracted sample weight from the original weight.

EXAMPLE VII

In Vitro Binding of Fiber

In vitro binding of alphacel and SWWB to [6,7-$^3$H (N)-$E_1$, [6,7-$^3$H(N)]-$E_2$, and [9,10-$^3$H (N)]-triolein was performed according to the method of Shultz and Howie (24). The isotopes were purchased from New England Nuclear/DuPont (Wilmington, Del.). Nonspecific binding for $^3$H $E_1$ was 1.25% for $^3$H $E_2$ 2.44% and for $^3$H triolein 32.56%. Background binding was subtracted to obtain net binding.

EXAMPLE VIII

Statistics

Statistical evaluations at the $p<0.01-0.001$ level using the chi-square test were made on the tumor incidence data and at the $p<0.05$ level using the Student's t-test on all other data.

EXAMPLE IX

Figure 2:
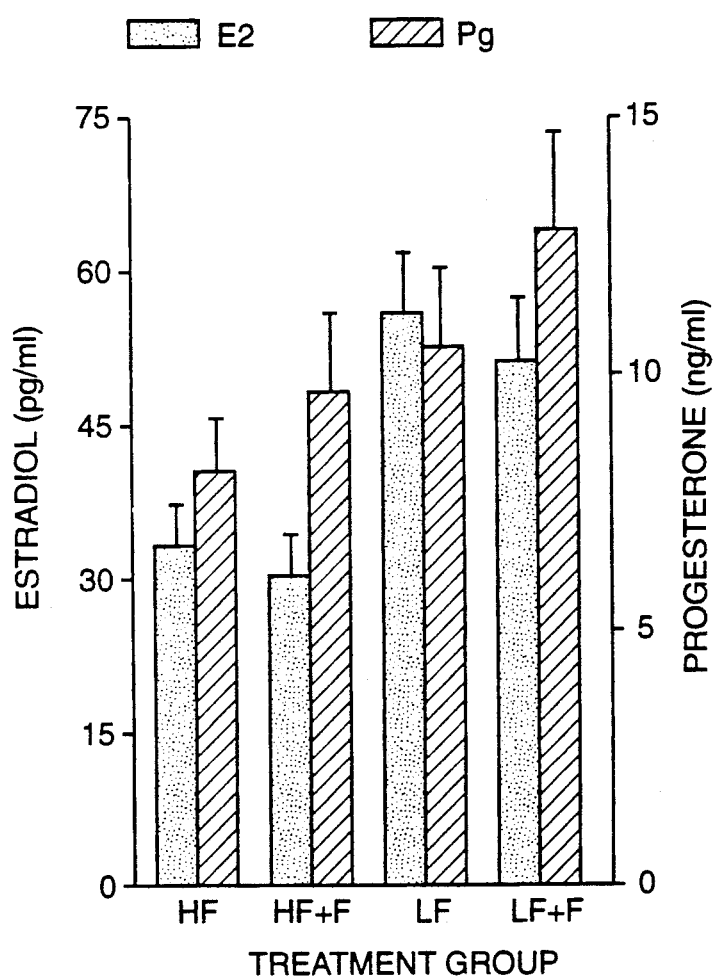
FIG. 2 Effect of dietary wheat bran supplementation on serum 17β-estradiol and progesterone levels. Serum was obtained from 16-24 rats/group at sacrifice and assayed by standard RIA methodology. Data points represent mean±SE. The four dietary groups were: HF=high fat (23.5% corn oil); HF+F =high fat plus fiber (10% soft white what bran); LF=low fat (5% corn oil); and LF+F=low fat plus fiber (10% soft white wheat bran). The LF and LF+F estradiol groups were significantly ($p<0.05$) greater than the HF and HF+F groups.
Figure 3:
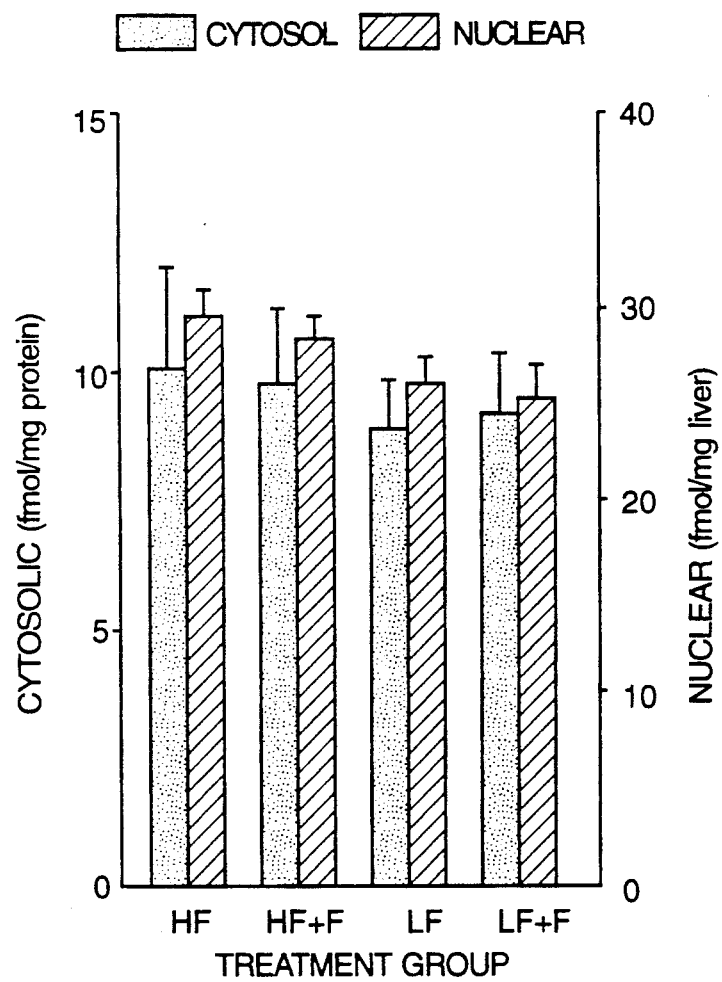
FIG. 3 Effect of dietary wheat bran supplementation on hepatic cytosolic and nuclear estrogen receptor protein levels. Livers were obtained from 18-20 rats/group at sacrifice and were assayed using the Abbott ER-EIA procedure. Data points represent mean±SE. The four dietary groups were: HF= high fat (23.5% corn oil); HF+F=high fat plus fiber (10% soft white wheat bran); LF=low fat (5% corn oil); and LF+F=low fat plus fiber (10% soft white wheat bran).

As reported earlier (18), the incidence of mammary tumors was significantly reduced in rats fed the HF+F diet compared to those on the unsupplemented HF diet. Addition of SWWB to the LF group resulted in a further nonsignificant decrease in tumor incidence compared to the unsupplemented LF group (FIG. 1). Supplemental SWWB had no significant effect on circulating 17β-estradiol or progesterone levels obtained at the time of sacrifice (FIG. 2). It was found that 17β-estradiol levels were significantly higher in the LF and LF+F groups compared to the HF and HF+F groups respectively. Hepatic cER and nER protein levels (FIG. 3) were similar in all four treatment groups.

Figure 5A:
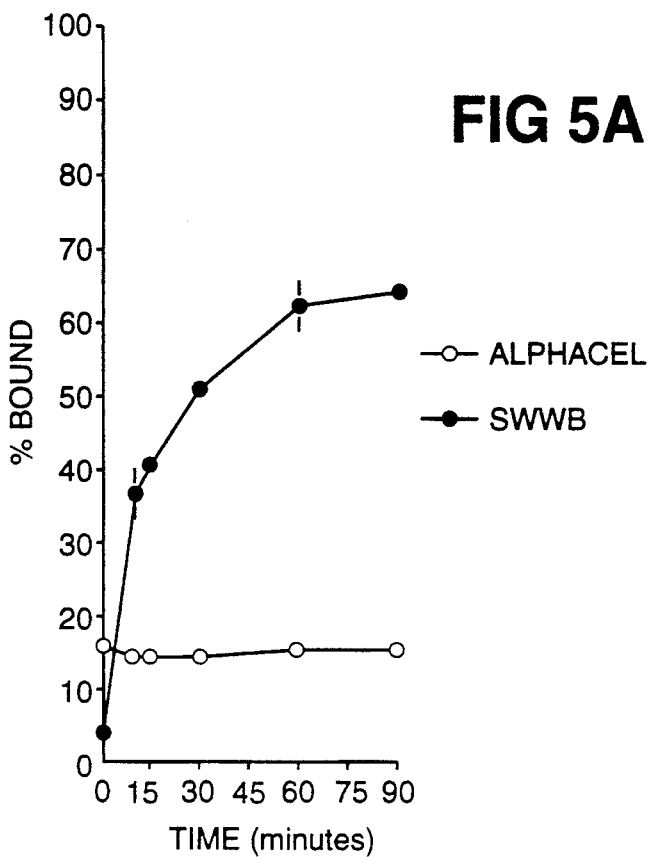
FIG. 5 Effect of dietary wheat bran supplementation on 24 hr fecal total ($E_1+E_2$) estrogen levels. Fecal samples (4/group) were obtained while the rats were in metabolism cages. Assays were performed using a kit obtained from ICN/RSL. Data points represent mean±SE. The four dietary groups were: HF=high fat (23.5% corn oil); HF+F=high fat plus fiber (10% soft white wheat bran); LF= low fat (5% corn oil); and LF+F=low fat plus fiber (10% soft white wheat bran).
Figure 5B:
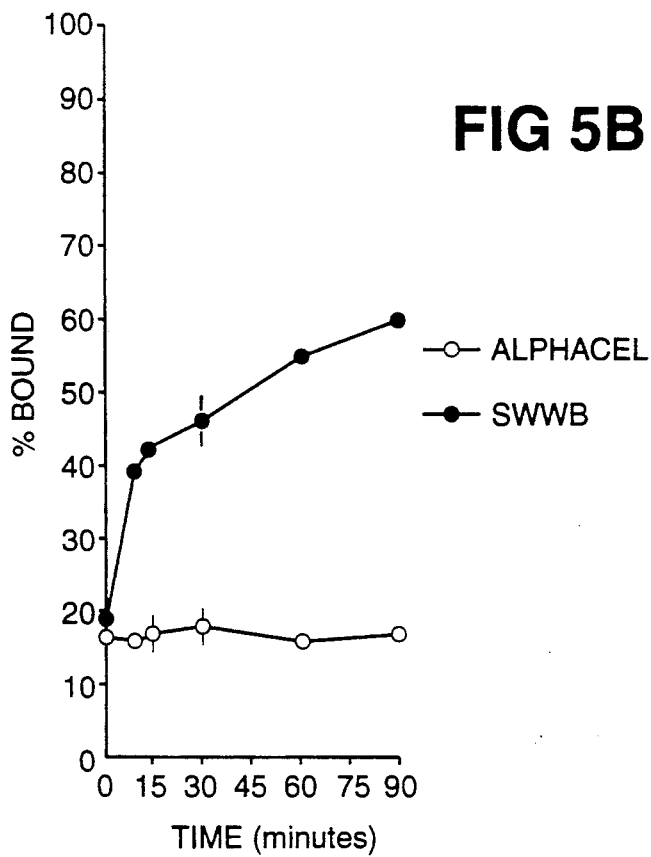
Figure 6:
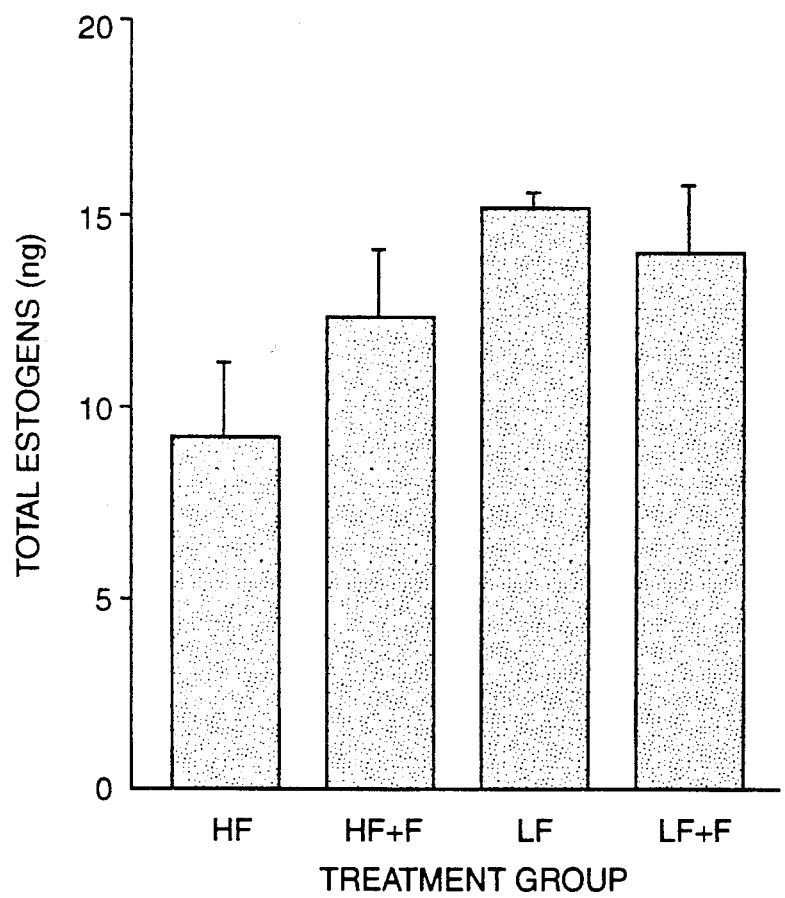
FIG. 6. Time course binding of $^3H$ estrone (upper panel) and $^3H$ estradiol (lower panel) to alphacel and SWWB. 50 mg of fiber was incubated with the labelled hormone for 0, 10, 15, 30, 60, and 90 minutes at 37° C. The percent of hormone bound was determined for each time point. Each data point represents the mean of three determinations±SE.

Reductions in total urinary estrogens in both fiber supplemented groups compared to their respective controls were observed (FIG. 4). We also found significant reductions in the amount of urinary estrogens excreted in the LF compared to the HF groups. The HF +F group exhibited a nonsignificant increase in total fecal estrogens compared to the HF alone group and the LF + F group was unchanged compared to the LF group (FIG. 5). Binding of $^3$H $E_1$ and $^3$H $E_2$ to alphacel and SWWB was rapid with significantly more hormone bound to SWWB than to alphacel at all time points (FIG. 6, upper and lower panel, respectively). Alphacel was found to consistently bind 15% of the radiolabelled hormone, whereas our the amount of hormone bound to SWWB increased over time from 5-15% at the start of the experiment to approximately 60-65% after a 90 minute incubation at 37° C.

Figure 7:
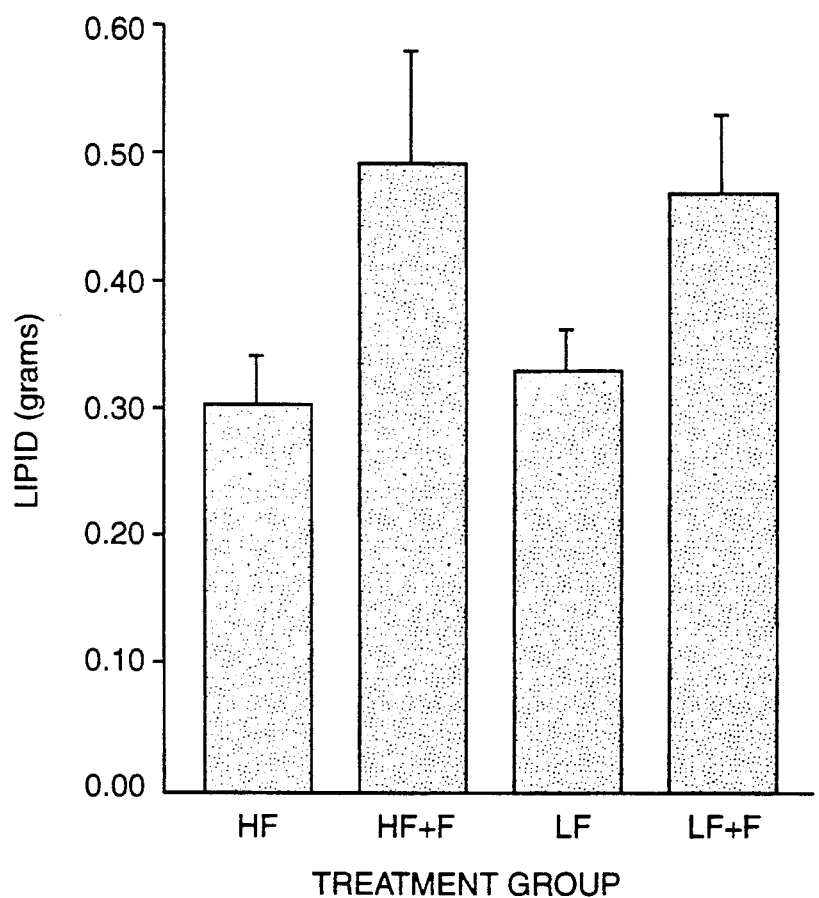
FIG. 7. Effect of dietary wheat bran supplementation on 24 hr fecal fat content. Fecal samples (4/group) were obtained while the rats were in metabolism cages. Assays were performed using standard Soxhlet extraction procedures. Data points represent mean±SE. The four dietary groups were: HF=high fat (23.5% corn oil); HF+F= high fat plus fiber (10% soft white wheat bran); LF=low fat (5% corn oil); and LF+F=low fat plus fiber (10% soft white wheat bran). The LF + F group was significantly ($p<0.05$) greater than the LF group.
Figure 8:
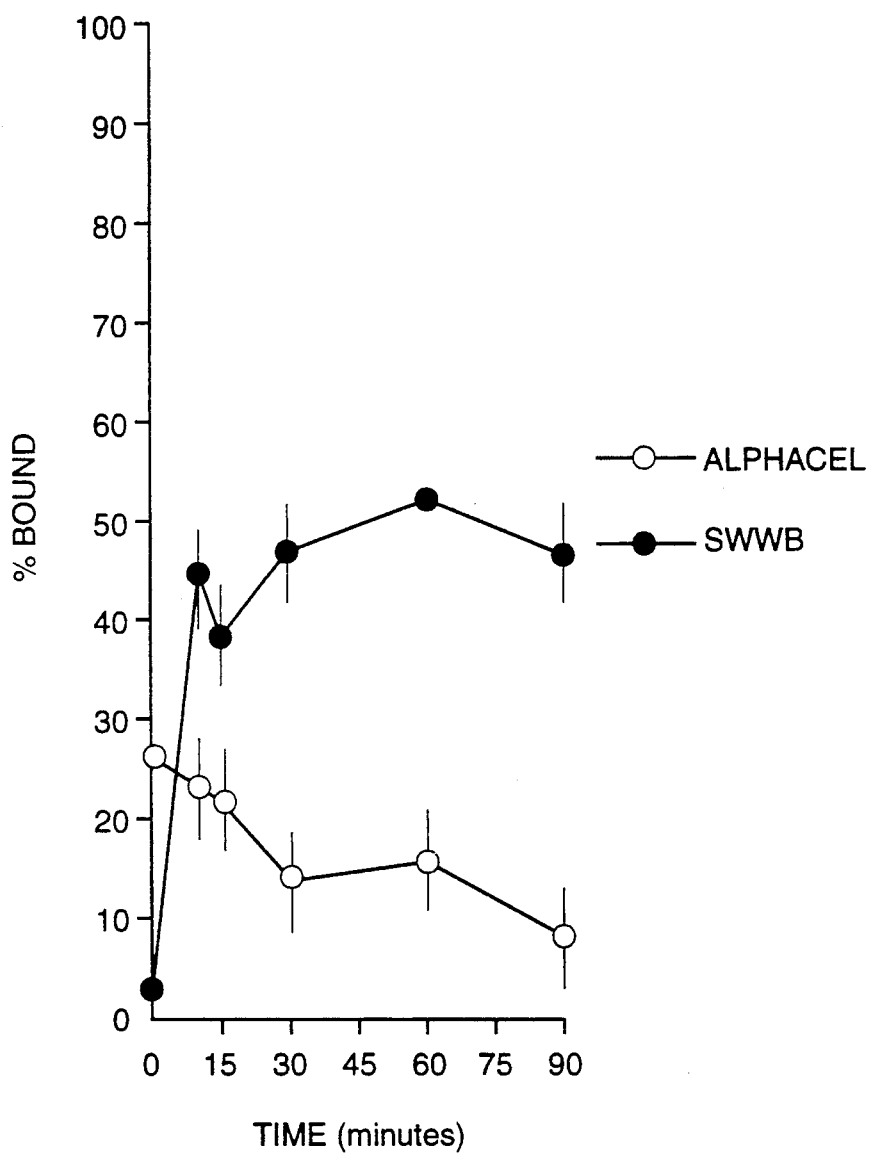
FIG. 8 Time course binding of $^3H$ triolein to alphacel and SWWB. 50 mg of fiber was incubated with the labelled triolein for 0, 10, 15, 30, 60, and 90 minutes at 37° C. The net percent of triolein bound was determined for each time point. Each data point represents the mean of five determinations±SE.

An increase in fecal lipid content of the HF+F group compared to the HF group, and a significant elevation in the lipid content of the LF+F group compared to the LF group were observed (FIG. 7). SWWB bound $^3$H triolein to a greater extent than alphacel (FIG. 8). Binding with alphacel decreased from 25% to 10% over time and for SWWB binding increased from 3% to approximately 50% during the course of the experiment.

The invention shows that the addition of 10% SWWB to the LF and HF diets not only lowered tumor incidence, but also altered the urinary excretion, and by implication, the enterohepatic recirculation of estrogens. In a recent study by Arts, et al. (25) female rats fed a high fiber (11% TDF from wheat bran) diet with fat consumption held constant were found to have a threefold higher level of fecal estrogens and decreased urinary $E_1$ (conjugated and unconjugated) levels compared to rats fed a low fiber (0.5% fiber from white wheat flour) diet. In addition, Arts, et al. (25) found an increase in serum $E_2$ levels at the peak (second day of diestrus and proestrus) of the estrus cycle in the fiber supplemented group, a result which apparently contradicts those reported in human studies. Also, in contrast to the present study, the authors reported that rats fed high and low fiber diets exhibited 90% and 80% mammary tumor incidence, respectively. It should be noted that the study by Arts, et al. (25) was designed to evaluate total carcinogenesis, whereas the previous results (18) dealt only with the post-initiation stage of carcinogenesis. Additionally, rats in the two studies were fed diets that differed in the type and amount of fiber, and therefore, their outcomes cannot be directly compared.

In an attempt to evaluate if dietary fiber exerted its protective effect by acting as an antiestrogen, as suggested by Adlercreutz (6-8), the effect of SWWB supplementation on several estrogenic parameters in the liver was assessed. The liver was chosen as a target organ rather than the mammary gland because it has been documented that human (26) and rat (27,28) livers are estrogen responsive organs and that the liver is well endowed with estrogen receptors (ER). Also, there is a paucity of glandular tissue in the normal mammary gland making it impractical for ER assays, while the liver provides an abundant and accessible source of experimental material. It has been shown that the antiestrogen tamoxifen given at a high dose in male rats (1.0 mg/day for 8 months) induced an accumulation of ER in the nucleus of hepatic cells (22). To test for the possible presence of antiestrogens in the SWWB supplement we therefore measured ER receptor protein content in the hepatic nucleus and cytosol. No change in hepatic ER status was found suggesting that SWWB is not acting as a source of antiestrogen at least at the quantities at which SWWB was ingested.

As noted earlier, a number of studies comparing serum, urinary, and fecal estrogen levels in vegetarians and nonvegetarians have been conducted (9-14). The rationale for these studies was that because vegetarians tend to consume more fiber and exhibit somewhat lower breast cancer rates than the general population, one could postulate a fiber induced decrease in the bioavailability of estrogens necessary for tumor development. In general, results of these studies suggest that urinary estrogen excretion is decreased and fecal estrogen excretion is increased in individuals consuming high fiber diets.

The present work finds that fiber supplementation alters the enterohepatic recirculation of estrogens in the direction of enhanced fecal and depressed urinary excretion patterns. However, along with Arts, et al. (25), we failed to see changes in serum estrogens concomitant with those found in human studies. The reason for the discrepancies between the rat and human studies is unclear, but may be due to inherent differences in the metabolism and disposition of estrogens in rodents and humans.

Other possible mechanisms that may account for the protective effect of SWWB are that: 1) estrogens physically bind to fiber and are removed in the feces and/or 2) fiber physically binds to lipid and removes it in the feces. The in vivo results indicate an increase in fecal estrogen excretion in the presence of fiber in the HF group and essentially no change in the LF group. In vitro binding results herein demonstrate that SWWB binds $E_1$ and $E_2$ to a greater extent than alphacel. The in vitro findings with SWWB are consistent with those of Shultz and Howie (24). It remains to be seen however, whether direct physical binding of estrogens to fiber in vivo is a major or minor determinant of fecal estrogen excretion. Our results in the rat model suggest that direct physical binding is not a major determinant. Regarding fecal lipid, it has been shown in humans (29,30) that increased fiber intake results in increased fecal lipid excretion regardless of the amount of fat ingested. Our results in the rat model are in close agreement with these studies. The in vitro binding results reported here also suggest that SWWB binds more readily and to a greater extent to $^3H$ triolein than does cellulose, and support the possibility that direct binding of lipid by SWWB may account for the increased fecal lipid excretion seen in fiber supplemented rats. The possibility, therefore, remains that fiber may act by creating a de facto LF condition by preventing lipid absorption in the small intestine.

The above findings were based on supplementation with one type of fiber, namely SWWB. This is a totally defined fiber as opposed to all other studies. Thus, it is not known if other types of fiber or mixtures of fibers, similar to that consumed by humans, have the same affect on reducing mammary tumor incidence and/or altering estrogen metabolism and excretion. Further studies using mixtures of different fiber sources at varying levels in the diet will be necessary to determine whether an overall increase in dietary fiber intake will provide protection against breast cancer. The first indications in that directions are shown here.

TABLE I

| Ingredients | Composition of semipurified diets* | | | |
| --- | --- | --- | --- | --- |
| | Group 1: 23.5% fat adjusted diet | Group 2: 23.5% fat diet + fiber supplement | Groupt 3: 5.0% fat diet | Group 4: 5.0% fat diet + fiber supplement |
| Casein, vitamin free, % | 23.50 | 20.0 | 20.0 | 17.0 |
| DL-Methionine, % | 0.35 | 0.27 | 0.3 | 0.25 |
| Corn Starch, % | 33.0 | 29.0 | 52.0 | 47.3 |
| Dextrose, % | 8.0 | 7.0 | 13.0 | 11.5 |
| Alphacel, % | 5.90 | 5.90 | 5.0 | 5.0 |
| Fiber supplement, % | — | 11.8 | — | 10.0 |
| Corn oil, % | 23.5 | 20.0 | 5.0 | 4.3 |
| Mineral mix, AIN-76A, % | 4.10 | 3.50 | 3.5 | 3.0 |
| Vitamin mix, AIN-76A, % | 1.7 | 1.5 | 1.5 | 1.3 |
| Choline bitartrate, % | 0.24 | 0.2 | 0.2 | 0.17 |
| Caloric density, kcal/g | 4.72 | 4.16 | 3.87 | 3.44 |

*Corn oil was added to the high-fat diets at the expense of starch and dextrose. The composition of diets was adjusted so that rats in the different dietary groups consumed approximately the same amount of protein, minerals, and vitamins, despite differences in caloric density.
Fiber = soft white wheat bran
This diet is based on the American Institute of Nutrition (AIN) standard reference diet (19) with modification of the source of carbohydrate.

REFERENCES

1. National Research Council, Committee on Diet and Health. Diet and Health. Implications for Reducing Chronic Disease Risk. Washington, DC, National Acad. Press, 1989.
2. Van't Veer, P., et al. Int. J. Cancer 45:825-828 (1990).
3. Rose, D.P., Cancer Surveys 5(3):671-687 (1986).
4. Lubin, F. et al. JNCI 77:605-612 (1986).
5. Rose, D.P., Nutrition and Cancer 13(1 and 2):1-8 (1990).

6. Adlercreutz, H., et al. Proceedings of the Symposium on the Analysis of Steroids. Eger, Hungary (1981).
7. Adlercreutz, H., Gastroenterology 86:761–766 (1986).
8. Adlercreutz, H., et al., Prog. Cancer Res. Ther. 35:409–412 (1988).
9. Armstrong, B.K., et al. JNCI 67:761–767 (1981).
10. Goldin, B.R., et al. Am. J. Clin. Nutr. 44:945–953 (1986).
11. Goldin, B.R., et al. N. Eng. J. Med. 307:1542–1547 (1982).
12. Gorbach, S.L., and Goldin, B.R. Prevent. Med. 16:525–531 (1987).
13. Fentiman, I.S., et al. Nutr. Cancer 11:101–106 (1988).
14. Barbosa, J.C., et al. Am. J. Clin. Nutr. 51:798–803 (1990).
15. Woods, M.W. et al. Am. J. Clin. Nutr. 49:1179–1183 (1989).
16. Heber, D., et al. Nutrition 7(2):137–140 (1991).
17. Rose, D.P., et al. Am. J. Clin. Nutr. 54:520–525 (1991).
18. Cohen, LA, et al. JNCI 83(7):496–501 (1991).
19. Department of Health, Education and Welfare, Guidelines for Carcinogen Bioassay in Small Rodents. DHEW Pub. No. (NIH) 76-801, Washington, DC, US Gov't. Print. Off., pp 1–65 (1976).
20. Chan, P.C., et al. JNCI 59:1279–1283 (1977).
21. Bieri, J.G., et al. J. Nutr. 107:1340–1348 (1977).
22. Kohigashi, K., et al. Jpn. J. Cancer Res. (Gann) 79:1335–1339 (1988).
23. Fotsis T., and Adlercreutz, H. J. Steroid Biochem. 28(2):203–213 (1987).
24. Shultz, T.D. and Howie, B.J. Nutr. Cancer 8:141–147 (1986).
25. Arts, C.J.M., et al. J. Steroid Biochem. Molec, Biol. 39(2): 193–202 (1991).
26. Porter, L.E., et al. Gastroenter. 84:704–712 (1984).
27. Aten, R.F., et al. Endocrinol. 131:1629–1635 (1978).
28. Powell-Jones, W., et al. J. Steroid Biochem. 13:219–229 (1980).
29. Southgate, D.A.T., and Durnin, J.V.G.A. Brit. J. Nutr. 24:517–535 (1970).
30. Kelsay, J.L., et al. Am. J. Clin. Nutr. 31:1149–1153 (1978).

We claim:

1. Method for altering the excretion of lipids in mammals comprising orally administering a diet containing sufficient wheat bran fiber to cause an increase in fecal excretion of lipids.

2. Method for altering the excretion of estrogens in mammals comprising orally administering a diet containing sufficient wheat bran fiber to cause an increase in fecal excretion of unconjugated estrogens and a decrease in urinary excretion of conjugated estrogens.

3. Method of claim 1 or 2 wherein the wheat bran is soft white wheat bran.

4. The method of claim 2 wherein the enterohepatic recirculation of estrogens is altered.

5. The method of claim 3 wherein soft white wheat bran binds lipid for increased fecal excretion of lipid.

6. The method of claim 3 wherein SWWB binds estrogen for increased fecal excretion of estrogen.

7. The method of claim 6 Wherein the estrogen is $E_1$ or $E_2$.

* * * * *